United States Patent [19]
Chiesi et al.

[11] Patent Number: 5,165,391
[45] Date of Patent: Nov. 24, 1992

[54] DEVICE FOR MOUTH-INHALING AEROSOL MEDICAMENTS

[75] Inventors: Paolo Chiesi, Fontanini di Vigatto; Isabella Panza, Parma; Paolo Ventura, Piacenza; Marco del Corno; Mario Varesco, both of Milan, all of Italy

[73] Assignee: Chiesi Farmaceutici S.p.A., Parma, Italy

[21] Appl. No.: 739,655

[22] Filed: Aug. 2, 1991

[30] Foreign Application Priority Data

Sep. 13, 1990 [IT] Italy ............................. 21457 A/90

[51] Int. Cl.⁵ .................................................. A61M 11/00
[52] U.S. Cl. ............................ 128/200.23; 128/200.14
[58] Field of Search .................... 128/200.14, 200.15, 128/200.16, 200.17, 200.18, 200.21, 200.23, 203.12, 203.15, 203.23

[56] References Cited

U.S. PATENT DOCUMENTS 4,174,712 11/1979 Moren et al. .................... 128/200.14
4,834,083 5/1989 Byram et al. .................... 128/200.23
4,953,545 9/1990 McCarty ........................ 128/200.23

FOREIGN PATENT DOCUMENTS 502074 5/1920 France ............................ 128/200.21
03419 3/1988 World Int. Prop. O. ...... 128/200.23

Primary Examiner—Clifford D. Crowder
Assistant Examiner—Stephen R. Funk
Attorney, Agent, or Firm—Oblon, Spivak, McClelland, Maier & Neustadt

[57] ABSTRACT

A device for mouth-inhaling medicaments dispensed as aerosols by pressurized cans. The device is flat and compact in shape, and includes a seat for housing a can and defines an expansion chamber into which the aerosol dispensed by the can, when operated, penetrates and expands to circulate with a vortex flow which causes the solvent to evaporate and the flow movement to continue for a relatively long time, hence enabling only very small particles of the medicament to be drawn into the bronchial tubes and lungs. There is only minimum aerosol particle deposition on the walls of the oropharingeal cavity, and inhalation can continue after the entry of aerosol into the expansion chamber ceases.

2 Claims, 2 Drawing Sheets

DEVICE FOR MOUTH-INHALING AEROSOL MEDICAMENTS

BACKGROUND OF THE INVENTION

1. Field of the Invention

This invention relates to a device for mouth-inhaling atomized medicaments dispensed by an aerosol can.

2. Discussion of the Background

Inhalation is the preferred system for administering medicaments (such as beta-2-stimulants, beta-adrenergics, antiallergic and anti-inflammatory agents) directed to the deepest parts of the respiratory tree in that it considerably reduces the dose compared with oral administration. It almost completely eliminates systemic side-effects and provides rapid onset of therapeutic action.

For this purpose pressurized cans containing the medicament and a propellant are used, the cans being provided with dispensers which when manually operated dispense measured quantities of atomized medicament through a nozzle.

Because of their ease of handling and the fact that they allow rapid and selective administration of the active principle, these cans have encountered considerable favor and are widely used both in maintenance therapy on chronic obstructive respiratory affections and in the treatment of acute asthmatic attacks.

Notwithstanding their apparent simplicity, common pressurized cans for dispensing measured quantities of aerosol are difficult to use correctly, as is confirmed by much scientific literature which states that most patients use them incorrectly either because they are unable to synchronize the dispensing action with their own inhalation and hence do not inhale the medicament at the correct moment, i.e. at the act of its delivery, which is violent and of very short duration, or because the patient does not maintain an adequate inhalation flow, or does not inhale sufficiently deeply, or for other reasons.

This problem becomes even more important in the case of certain patients such as children, the elderly and patients with reduced respiratory or manual capability.

Even if a dispensing can for aerosol medicaments is used correctly, the availability of an inhaled medicament to the air passages depends largely on the size of the aerosol droplets (propellant droplets covering medicament particles), which is governed by the formulation, and on the propellant evaporation time.

It is in any event well documented that even under the most favorable conditions only 10% of the aerosol dose dispensed by a pressurized can reaches the air passages. A similar percentage is expired or is deposited outside the oral cavity, whereas because of the impact of the high speed particles about 80% is deposited within the oropharyngeal cavity, is swallowed and absorbed at the systemic level (and hence practically lost).

The quantity of medicament inhaled is however usually sufficient to achieve the pharmaceutical effect.

However, if the pressurized can is not used in the appropriate manner the quantity of medicament which reaches the site of action at the pulmonary level is further reduced and the therapeutic response is compromised.

Excessive medicament depositing in the oropharyngeal cavity can also lead to undesirable effects either at the systemic level as a consequence of the medicament absorption, or at the local level, as in the case of corticosteroids, which can result in oral candidiosis. In an attempt to overcome the problems connected with the direct use of cans for dispensing measured quantities of atomized medicament, devices have been developed over the last decade for application to the nozzles of pressurized dispensing cans. Depending on their dimensions these devices can be classified as either "spacers" or actual "expansion chambers".

In practice, the "spacer" devices are tubes to be interposed between the can dispensing nozzles and the mouth of the user to improve the amount of deposition of the medicament at the pulmonary level by intervening on two factors, namely the size of the aerosol droplets and their impact within the orophangeal cavity.

In this respect, the period between the dispensing of the spray and its inhalation allows rapid evaporation of the propellant and a resultant decrease in the size of the particles before they enter the respiratory tree, thus favoring improved penetration as far as the lower air passages.

Again, the space which the "spacer" device interposes between the dispensing nozzle and the patient's mouth facilitates the evaporation of the propellant vapor and decreases the particle speed, so reducing the percentage of medicament lost due to immediate impact with the oral cavity.

Finally, the quantity of inhaled propellant is reduced, with consequent greater pleasantness for the user and a lessening of risks connected with its possible toxicity.

The "spacer" devices of the aforesaid type have the common characteristic of a substantially cylindrical shape and a fairly small volume (70–100 ml).

The use of this type of "spacer" device has rapidly become extensive as an aid to those patients who are unable to properly use the common cans for dispensing measured quantities of aerosol or who have difficulty in understanding the rather complicated instructions.

Evidence from the scientific literature shows however that the addition of small "spacers" does not produce appreciable improvement at the clinical level.

For this reason research in this sector has been orientated towards the perfection of devices in the form of actual large-volume expansion chambers.

Besides possessing the advantages attributed to the "spacer" devices, these "expansion chambers" should contribute to resolving the considerable problem of lack of coordination between the dispensing action and the inhaling action, because they enable the intake to be delayed by a few seconds after delivery, hence aiding patients with more serious respiratory difficulties.

However, known "expansion chambers" have considerable drawbacks which hinder their use and acceptability. In this respect, as the aerosol jet is sprayed into the cavity defined by said chambers, the aerosol droplets strike the chamber walls to then diffuse into the central region of the chambers. A large number of the medicament droplets tend to deposit on the chamber walls and are lost. To reduce this problem, the known "expansion chambers" are of large size (for example about 750 ml), making their portable use practically impossible and creating storage problems for the factory and pharmacy. An expansion chamber of this type is described in GB patent 1,565,029.

SUMMARY OF THE INVENTION

The main object of this invention is to provide a mouth-inhaling device usable with pressurized cans for dispensing measured quantities of medicament, the inhaler device being of low cost, small overall size to facilitate factory and pharmacy storage and to enable it to be contained in a handbag or jacket pocket, portable, simple to use, and very simple to fit to a pressurized can. Said device is designed to favor the inhaling of a greater number of active component particles and to avoid spraying the aerosol directly onto the mucosa of the oropharynx in order to safeguard the user against side-effects derived from direct spray into the mouth. In this respect, the device has an expansion chamber shaped to create, by virtue of the speed at which the atomized material is expelled by the dispenser, a vortex flow in which the particles remain in suspension for a time sufficient to discharge their kinetic energy and allow substantial evaporation of the propellant, with a consequent reduction in the size of the particles, which can hence be more easily drawn into the bronchial tubes and lungs of the patient, while any large size particles are centrifuged onto the walls of the chamber, to deposit on them.

The invention therefore provides a device for mouth-inhaling medicaments dispensed as aerosols by pressurized cans, comprising a body with a seat for housing a can provided with a stem for operating the can dispensing valve, a chamber for the collection and expansion of the aerosol dispensed by a discharge nozzle on the can, and an inhalation mouthpiece communicating with said chamber and projecting outwards from said body, characterized in that said body is of a substantially flat shape, said chamber being delimited by a curved wall, into a first peripheral portion of which there opens the inner end of said mouthpiece, and in a second peripheral portion of which, opposite the first, there is an aperture from which two walls extend outwards from the chamber to converge towards the can discharge nozzle and define a duct the central plane of which is inclined to the central plane of said mouthpiece, in such a manner as to generate within said chamber a vortex in the aerosol discharged by the can.

BRIEF DESCRIPTION OF THE DRAWINGS

The structure and characteristics of the inhaler device will be more apparent from the description of a preferred embodiment thereof given by way of non-limiting example with reference to the accompanying drawings, in which.

DESCRIPTION OF THE PREFERRED EMBODIMENTS

The inhaler device shown in the figures is of a decidedly flat shape. It is formed from two specular shells 1 and 2 which can be joined together by simple pressure by the provision of holed appendices and pegs 12 provided on the inside of the shell 1 and shell 2 respectively (FIG. 2).

Figure 2:
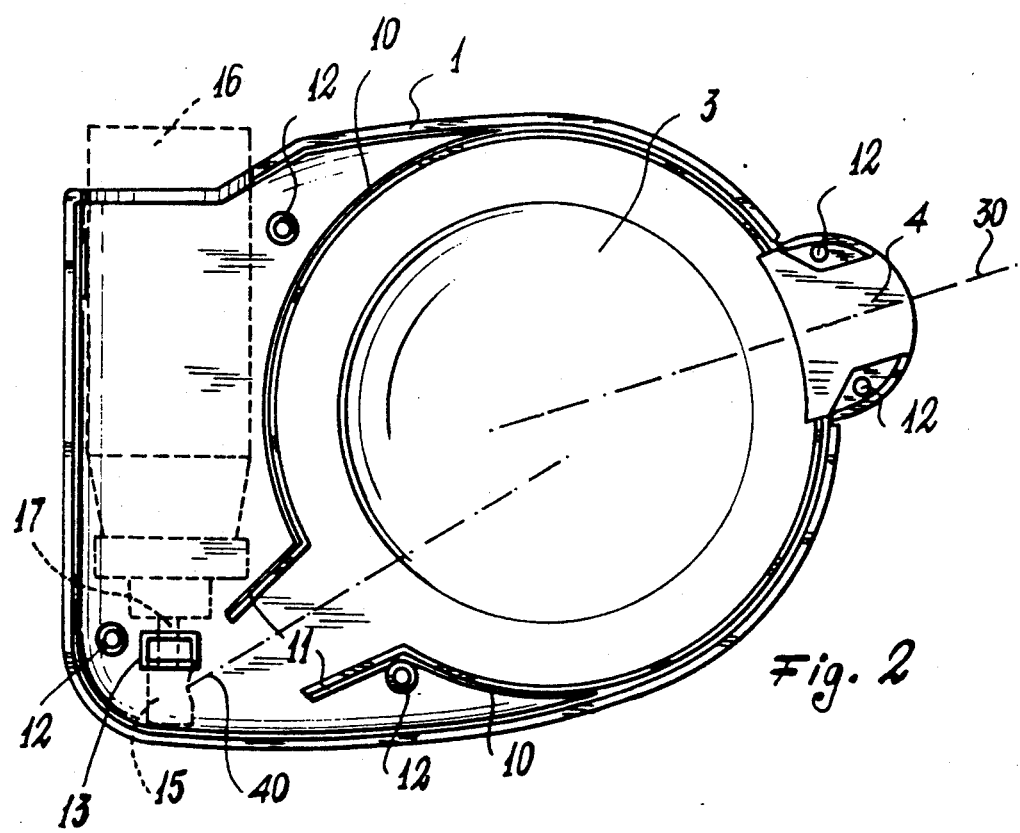
FIG. 2 shows one of the two shells forming the device, viewed in the direction indicated by the lines 2—2 of FIG. 1.
Figure 3:
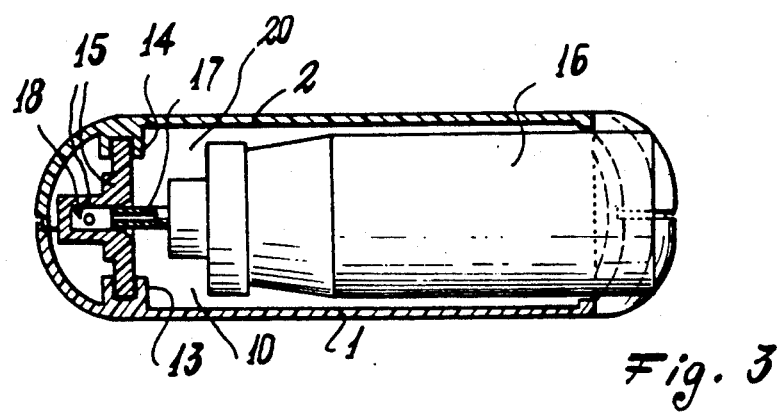
FIGS. 3 and 4 are sectional views taken through the inhaler device along lines 3—3 and 4—4 of FIG. 1.
Figure 4:
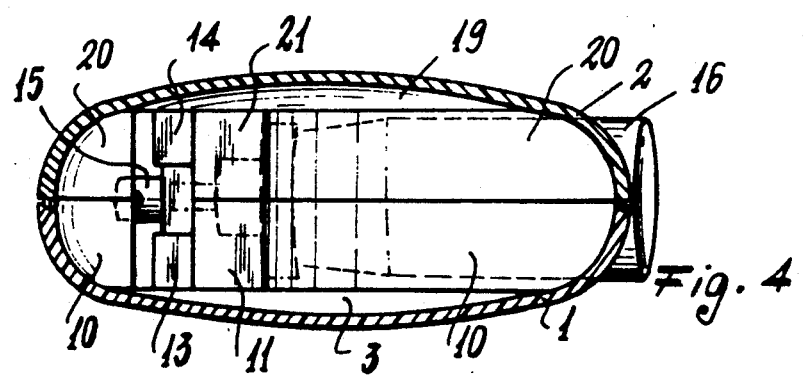

A curved wall 10 projects inwards from the shell 1 (FIGS. 1 to 3), whereas a curved wall 20, specular to the wall 10, projects inwards from the shell 2 (FIGS. 3 and 4). When the two shells 1 and 2 have been joined together, the two walls 10 and 20 define with the two shells an expansion chamber, at which the two shells comprise outwardly projecting convex portions 3, 19 for the purpose of increasing the chamber area.

A mouthpiece projects from a first peripheral portion of the walls 10, 20 and is defined by two appendices 4, 5 projecting from the shells 1 and 2 respectively. The two appendices 4, 5 define a passage 6 the inner end of which opens into said chamber.

It can be seen from FIG. 2 that in a second peripheral portion of the curved wall 10, 20 opposite that from which the mouthpiece 4, 5 projects there is an aperture from which two walls 11 and respectively 21 (FIG. 4) extend outwards from the chamber to converge (FIG. 2) towards the exit hole of a shaped nozzle 15 having nozzle head 18 housed and retained in two seats 13 and 14 projecting from the shells 1 and 2 respectively.

The body 1, 2 also defines a seat, external to the expansion chamber, which can receive by axial insertion a can 16 of known type (shown by dashed lines in FIG. 2), provided with a hollow stem 17 which is inserted and retained in a seat provided in the shaped nozzle 15. The can is preferably of the pressurized type for emitting measured quantities of aerosol each time the stem 17 is pushed, and it can be seen that that end of the can distant from the end provided with the stem projects outside the body 1, 2. Finally, it should be noted that the center plane 30 through the mouthpiece 4, 5 is inclined to the center plane 40 between the convergent walls 11, 21, these center planes being shown by dashed and dotted lines in FIG. 2.

When the pressurized can 16 has been housed in its housing in the body 1, 2, with the stem 17 inserted into the seat of the shaped nozzle 15, the body 1, 2 can be gripped with one hand, the mouthpiece 4, 5 placed in the mouth and the base of the can 16 pressed with one finger, the stem remaining fixed and at rest in the nozzle 15. This results in the opening of the dispensing valve within the can, from which a measured quantity of aerosol emerges through the open end of the hole in the nozzle 15, to pass between the diverging walls 11, 12 and penetrate into the expansion chamber delimited laterally by the curved walls 10, 20, which are shaped to impose on the aerosol jet a vortex motion which results in deposition of the largest particles on the walls 10, 20 whereas the other particles lose their layer of propellant and hence reduce in diameter.

Although the spray dispensed by the can is very violent and of very short duration, the aerosol mass which expands and rotates with vortex motion within the expansion chamber remains in movement for a considerably longer time than the duration of discharge from the can.

Because of its particular constructional characteristics the inhaler device of the present invention can perform the double function of protracted transfer dispenser and spacer, so satisfying the various treatment requirements and adapting to the needs of the patient.

In this respect, the patient can remove the cover and insert the mouthpiece 4, 5 into his mouth at the moment of dispensing, or alternatively he can operate the dispenser with the device closed and only then remove the cover and insert the mouthpiece into his mouth.

In either case, the patient can repeatedly inhale the aerosol, the droplets of which are of very small size and can thus reach deep into the bronchial tubes and lungs, whereas only a minimum quantity of such droplets deposits on the walls of the oral cavity.

Figure 1:
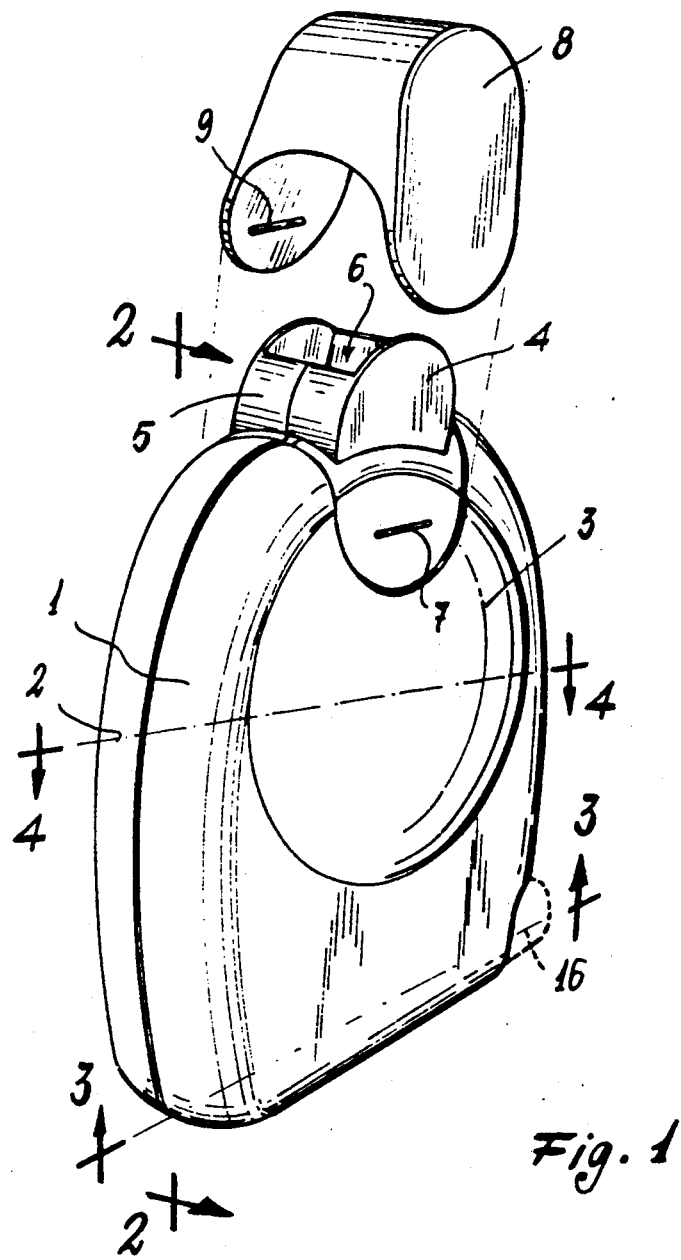
FIG. 1 is a perspective view of the inhaler device.

Hence it can be seen that the described inhaler device (provided with a cover 8 for the closure and protection of the mouthpiece 4, 5, on which it is retained by engagement between the projections 9 and the projections 7 shown in FIG. 1) is of very simple and economical structure and of minimum bulk, so that it can be carried in a handbag or in a jacket pocket.

It also gives the aerosol jet emitted by the can a vortex flow within a small-dimension expansion chamber, so that the highest number of small-dimension particles practically free from propellant follow the direction of flow of the inhaled air, limiting the undesirable side-effects deriving from direct spraying onto the oropharynx mucosa.

The can is easily fitted and removed and the device can be easily washed. In a further embodiment of the invention the can could be immovably inserted into a seat provided in the device and the aerosol be dispensed by operating a pushbutton or the like which acts directly on the stem or dispenser on the can.

We claim:

1. A device for mouth-inhaling a medicament dispensed as an aerosol by a pressurized can, comprising:
- a pressurized can having a discharge nozzle,
- a body, said body comprising:
- a seat for housing said pressurized can,
- a chamber within said body, adjacent said seat, for collection and expansion of said aerosol dispensed by said can,
- a inhalation mouthpiece communicating with said chamber through an inner end projecting outwardly from said body,
- wherein, said body is of substantially flat shape, said chamber is delimited by a curved peripheral wall, said inner end of said mouthpiece communicates with said chamber through a first opening in said curved peripheral wall at a first location, said curved peripheral wall bearing a second opening at a second location opposite said first location,
- opposed walls extending outwardly from said second opening toward said discharge nozzle to define a duct, such that a center plane passing through a center portion of said duct is inclined to a center plane passing through a center portion of said mouthpiece,
- such that within said chamber a vortex is created in said aerosol dispensed by said pressurized can.

2. The device of claim 1, wherein said seat permits axial movement of said pressurized can in said body, said pressurized can comprises a valve means which, when opened, allows said aerosol to pass to said discharge nozzle,
- said pressurized can depressibly protruding from said body when not in use,
- such that said valve means is opened by depressing said pressurized can into said body.

* * * * *